United States Patent
Holland

(10) Patent No.: US 11,810,215 B2
(45) Date of Patent: Nov. 7, 2023

(54) SYSTEM AND METHOD FOR PUBLIC HOUSING EVALUATION

(71) Applicant: Morgan State University, Baltimore, MD (US)

(72) Inventor: Jacqueline M. Holland, Mount Rainier, MD (US)

(73) Assignee: Morgan State University, Baltimore, MD (US)

( * ) Notice: Subject to any disclaimer, the term of this patent is extended or adjusted under 35 U.S.C. 154(b) by 0 days.

(21) Appl. No.: 18/056,826

(22) Filed: Nov. 18, 2022

(65) Prior Publication Data

US 2023/0082146 A1 Mar. 16, 2023

Related U.S. Application Data

(63) Continuation of application No. 16/923,187, filed on Jul. 8, 2020, now abandoned.
(Continued)

(51) Int. Cl.
*G06Q 50/22* (2018.01)
*G06Q 50/26* (2012.01)
(Continued)

(52) U.S. Cl.
CPC ......... *G06Q 50/22* (2013.01); *G06F 16/2465* (2019.01); *G06Q 30/0203* (2013.01);
(Continued)

(58) Field of Classification Search
CPC ........ G06Q 10/00–50/00; G16H 10/00–80/00; G06F 1/00–2221/00
(Continued)

(56) References Cited

U.S. PATENT DOCUMENTS 8,005,724 B2 * 8/2011 Dunning ............ G06Q 30/0269
705/26.7
10,445,809 B2 * 10/2019 Dunning ............ G06Q 30/0627
(Continued)

OTHER PUBLICATIONS

Ibem, Eziyi Offia, and Egidario B. Aduwo. "Assessment of residential satisfaction in public housing in Ogun State, Nigeria." Habitat International 40 (2013): 163-175. (Year: 2013).*
(Continued)

*Primary Examiner* — Alan S Miller
(74) *Attorney, Agent, or Firm* — Whiteford, Taylor & Preston, LLP; Gregory M. Stone; Lisa M. Schreihart

(57) ABSTRACT

Disclosed herein is a system and method for public housing evaluation including a computer-implemented public housing evaluation unit that receives survey data from a remotely connected survey device. The survey data comprises information about the physical environment of one or more public housing residents that is used to create a digital public housing environment profile for each survey participant. A plurality of digital public housing environment profiles may be statistically analyzed to create a public housing index identifying interrelationships among physical environment and demographic data in the digital public housing environment profiles. Public housing authority computers may access and view the public housing index to determine whether actions may be taken that may improve a public housing resident's physical environment and/or likelihood that they may successfully transition out of public housing.

20 Claims, 3 Drawing Sheets

Related U.S. Application Data

(60) Provisional application No. 62/871,342, filed on Jul. 8, 2019.

(51) Int. Cl.
| | |
|---|---|
| *G06Q 30/0203* | (2023.01) |
| *G16H 50/70* | (2018.01) |
| *G06F 16/2458* | (2019.01) |
| *G06Q 30/0204* | (2023.01) |
| *G06Q 50/16* | (2012.01) |

(52) U.S. Cl.
CPC ......... *G06Q 30/0204* (2013.01); *G06Q 50/26* (2013.01); *G16H 50/70* (2018.01); *G06F 2216/03* (2013.01); *G06Q 50/163* (2013.01)

(58) Field of Classification Search
USPC .............................................. 705/7.11–7.42
See application file for complete search history.

(56) References Cited

U.S. PATENT DOCUMENTS

| | | | | |
|---|---|---|---|---|
| 2002/0082901 | A1* | 6/2002 | Dunning | G06Q 30/0631 |
| | | | | 705/14.69 |
| 2011/0076663 | A1* | 3/2011 | Krallman | G09B 7/00 |
| | | | | 434/362 |
| 2013/0138555 | A1* | 5/2013 | Shishkov | G06Q 40/03 |
| | | | | 705/38 |

OTHER PUBLICATIONS

Ibem, Eziyi O., Pearl A. Opoko, and Egidario B. Aduwo. "Satisfaction with neighbourhood environments in public housing: evidence from Ogun State, Nigeria." Social Indicators Research 130.2 (2017): 733-757. (Year: 2017).*

* cited by examiner

SYSTEM AND METHOD FOR PUBLIC HOUSING EVALUATION

CROSS REFERENCE TO RELATED APPLICATIONS

This application is a continuation of U.S. application Ser. No. 16/923,187 titled "SYSTEM AND METHOD FOR PUBLIC HOUSING EVALUATION," filed with the United States Patent and Trademark Office on Jul. 8, 2020, which is based upon and claims the benefit of U.S. Provisional Application No. 62/871,342 titled "Framework for Public Housing Index," filed with the United States Patent & Trademark Office on Jul. 8, 2019, the specifications of which are incorporated herein by reference in their entireties.

FIELD OF THE INVENTION

This invention is directed to systems and methods for evaluating public housing, and more particularly to computer-implemented systems and methods for creating an adaptive and dynamic public housing index based on public housing residents' and administrators' perceptions of their public housing environment, which index may be accessed by housing authorities to assess the public housing environment and provide insight into the future possibility of individuals being able to live outside of public housing, or improve the current state and quality of life inside of public housing complexes.

BACKGROUND OF THE INVENTION

The United States Department of Housing and Urban Development ("HUD") approximates that there are about 30 million households in the United States that possess indoor environmental hazards, including by way of non-limiting example lead-based paint, mold, water leaks, and pests, among others. These conditions create housing that is substandard and negatively impacts the health of the residents. In an effort to meet such challenges, HUD's Healthy Homes program concentrates on eliminating dangerous and toxic items from the public housing environment, such as pests, contaminants, allergens, and hazards, all of which can cause injury that can result in challenges to well-being. The model of Healthy Homes is a way to address concerns regarding the relationship between the house and its interior environment. Addressing this issue is imperative to ensuring good health among public housing residents, as health challenges are often associated with a person's home interior and exterior surroundings.

Of course, ensuring safe environments for approximately 30 million households in the United States is quite a challenge, even for an agency of the federal government. Limited tools are available to readily assess public housing environments, much less to analyze those environments to determine how different environmental factors might impact one another and possibly synergistically affect, whether possibly or negatively, the health of public housing residents, and to enable public housing authorities to access such data so that interventions may be planned to improve those environmental factors, and to likewise plan for a resident's ultimate move out of public housing.

Thus, there remains a need in the art for systems and methods capable of collecting critical data reflecting public housing residents' environment, evaluating that data to determine interrelationships among environmental factors, and allowing access to housing authorities for purposes of interventional planning.

SUMMARY OF THE INVENTION

Disclosed herein is a system and method for public housing evaluation that avoids one or more disadvantages of the prior art. A system as described herein includes a computer-implemented public housing evaluation unit that receives survey data from a remotely connected survey device. The survey data comprises information about the physical environment of one or more public housing residents to create a digital public housing environment profile for each survey participant, which may include data such as the survey participant's individual observations of crime impacting a particular public housing facility, overall health of residents of a particular public housing facility and/or individual unit, physical environment of the particular public housing facility and/or individual unit, aging of building infrastructure for the particular public housing facility and/or individual unit, cleanliness of the particular public housing facility and/or individual unit, intergenerational relationships among residents, education levels of residents, and employment status of residents, although other factors may likewise be included without departing from the spirit and scope of the invention.

More particularly, each of those foregoing high-level categories of public housing environment survey data may themselves comprise a variety of more detailed questions that elicit more specific data describing the public housing environment, including by way of non-limiting example data that describes interior structure, water supply, plumbing condition, heating condition, air conditioning availability and condition, condition of outside areas, existence and condition of laundry accommodations, existence and condition of storage accommodations, existence and condition of appliances, ventilation condition, electrical condition, general property safety, public transportation accessibility, timeliness of the handling of complaints by public housing residents, timeliness of handling concerns of public housing residents, and an individual public housing resident's sense of community with other residents.

In addition to the collection of such public housing environment data, particularly in the case where the survey participant is an individual public housing resident, the survey information may include individual resident profile information, including by way of non-limiting example employment status, income, education level, gender, age, and zip code, practice setting in which the survey is administered (e.g., secondary education facility, post-secondary education facility, governmental administrative office, community center, business facility, etc.), how long the individual public housing resident has lived at the particular public housing facility, and the number of people in the residence. Such survey information may also be supplemented with publicly available public housing information.

All of the foregoing data may then be compiled in a digital public housing environment profile for each survey participant. A housing factor interrelationship analysis engine may then analyze the collection of such digital public housing environment profiles over time in order to statistically determine relationships among the varied public housing environment data and compile them in a public housing index to aid public housing administrators in determining interventions that might improve the living situation for residents of public housing, and that may enable such public housing administrators to determine whether individual public housing residents are able to transition out of public housing.

The housing factor interrelationship analysis engine may modify and recalibrate the public housing index based on the continuous collection of survey results and the continuous application of various analytical methods to identify interrelationships among the environmental factors that impact the lives of public housing residents.

In accordance with certain aspects of an embodiment of the invention, a computer implemented method is disclosed for evaluating public housing, comprising the steps of: providing a public housing evaluation unit having a processor and a memory; providing a survey device in data communication with the public housing unit; receiving at the public housing evaluation unit from the survey device a digital public housing environment profile associated with a human survey participant; analyzing at the processor of the public housing evaluation unit the digital public housing environment profile in combination with at least one stored digital public housing environment profile to identify one or more interrelationships among physical environment and demographic data in the digital public housing profiles; and storing in the memory a public housing index including a graphical or tabular depiction of the interrelationships among the physical environment and demographic data in the digital public housing profiles.

In accordance with further aspects of an embodiment of the invention, a computer system is disclosed for evaluating public housing, comprising: a public housing evaluation unit having a processor and a memory; and a survey device in data communication with the public housing evaluation unit; wherein the processor of the public housing evaluation unit includes computer instructions configured to receive at the public housing evaluation unit from the survey device a digital public housing environment profile associated with a human survey participant, analyze at the processor of the public housing evaluation unit the digital public housing environment profile in combination with at least one stored digital public housing environment profile to identify one or more interrelationships among physical environment and demographic data in the digital public housing profiles; and store in the memory a public housing index including a graphical or tabular depiction of the interrelationships among the physical environment and demographic data in the digital public housing profiles.

Still other aspects, features and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The numerous advantages of the present invention may be better understood by those skilled in the art by reference to the accompanying drawings in which.

DETAILED DESCRIPTION

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced items.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Figure 1:
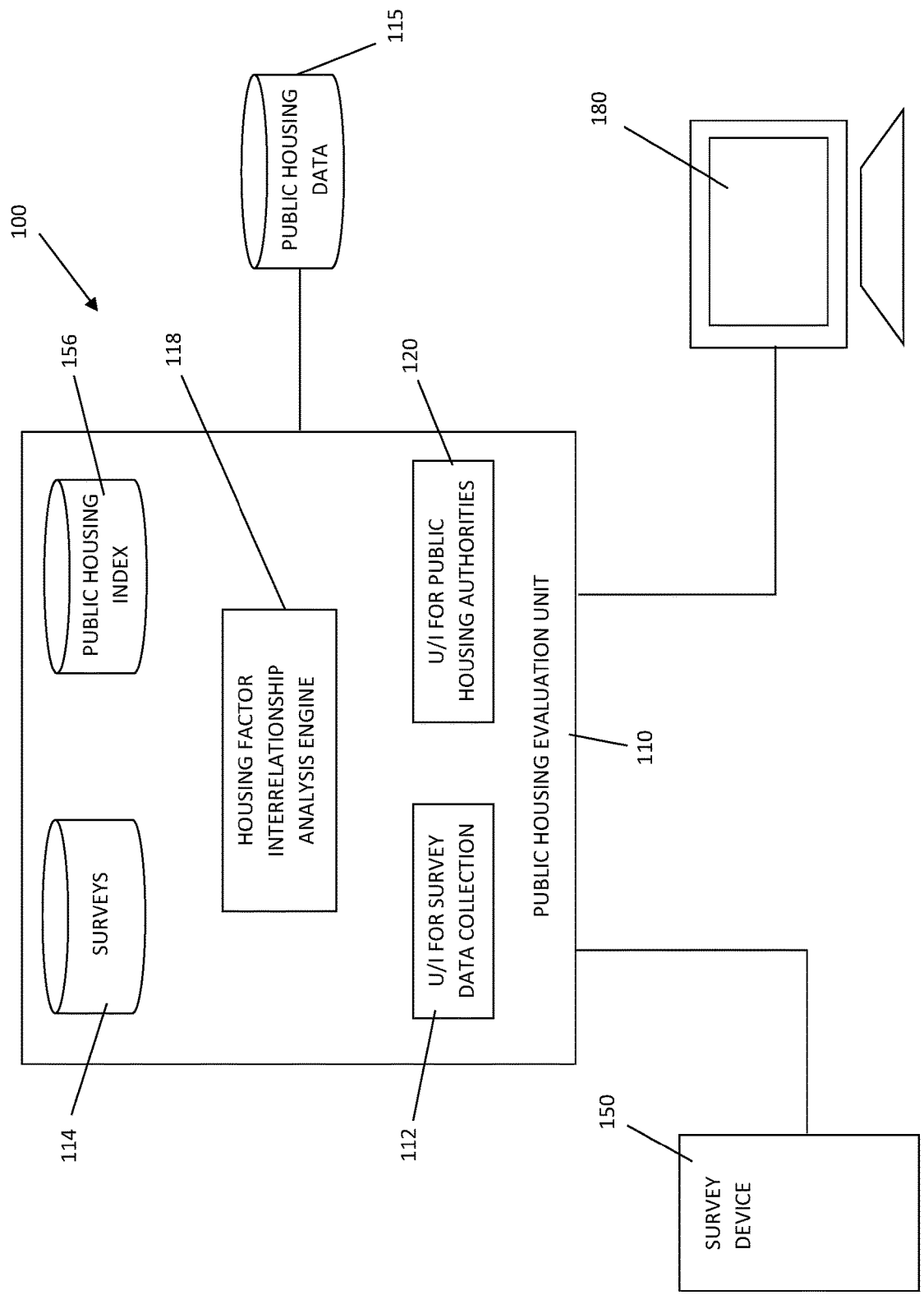
FIG. 1 is a schematic view of a system for public housing evaluation in accordance with certain aspects of an embodiment of the invention.

FIG. 1 shows an exemplary schematic representation of a system for evaluating public housing (shown generally at 100) including a public housing evaluation unit 110, one or more computer implemented remote survey devices 150 in remote data communication with public housing evaluation unit 110, and one or more public housing administrator computers 180 in data communication with public housing evaluation unit 110. Public housing evaluation unit 110 is preferably a hosted system that may, by way of non-limiting example, be hosted in a cloud processing environment accessible via a wide area data network such as the Internet.

Survey device 150 is preferably a remote computing device, such as a tablet, a laptop computer, a smartphone, or similarly configured readily portable computing device, configured for remote communication with public housing evaluation unit 110. Survey device 150 is used to record responses from one or more individuals that have knowledge of the physical public housing environment and may include by way of non-limiting example public housing residents, individuals at offices of public housing agencies, academic members, and policy makers. Public housing evaluation unit 110 preferably hosts a user interface 112 for survey data collection, which preferably receives a login request from survey device 150 and authenticates the user (e.g., through password entry or other such authentication methods as may be chosen by those skilled in the art) to public housing evaluation unit 110. Public housing evaluation unit 110 may receive a request from survey device 150 for a survey from survey database 114 and may transmit a digital survey to survey device 150 for administering to the survey participant. The digital survey includes survey questions as described above that solicit the survey participant's observations of the physical public housing environment and may optionally additionally include the above-described demographic data relating to that individual survey participant (particularly where the survey participant is an individual public housing resident). Of course, other environmental and demographic data beyond that described above may be included in the digital survey as may be preferable for a given population, which may be readily determined by persons skilled in the art.

The data collected by the digital survey may form a digital public housing environment profile that may be transmitted from survey device 150 to public housing evaluation unit 110 through user interface 112, and public housing evaluation unit 110 may generate and store in data memory an individual digital public housing environment profile for the survey participant. Optionally, public housing evaluation unit 110 may supplement the survey participant's individual digital public housing environment profile with existing public data 115 that may be geospatial in nature (e.g., publicly available community demographic data), which may be helpful to further determine interrelationships among various environmental and demographic factors that may affect the health of the public housing environment.

Using statistical analytical methods as may be selected and customized by those skilled in the art, a housing factor interrelationship analysis engine 118 may analyze the digital public housing environment profiles of multiple survey participants and may generate a public housing index 156. Weights that are assigned among real and perceived environmental factors and their subcategories, and among profile data and its associated subcategories, may readily be adjusted by those skilled in the art, and may thus be adapted to more conclusively establish the interrelationships between factors in the public housing index 156. Moreover, data comprising the public housing index 156 may be analyzed using a combination of statistical tests as are known by and may be readily selected and configured by those skilled in the art, to single out the greatest potential of interrelationships that would suggest some intervention to improve the public housing resident's physical environment and/or their ability to transition out of public housing. In certain configurations, the data collected in public housing index 156 may be expressed as a cumulative figure for one or a particular group of digital public housing environment profiles, and may likewise be sorted with respect to each factor embodied in the digital public housing environment profile, by geographical area, by time, or through a combination of factor, geography, and time.

Public housing index 156 may further be displayed in tabular form or graphically, such as in a "heat map" or the like, and in a Geographical Information System (GIS), or in such other visual presentation as may be preferred by those skilled in the art. For example, mapping features including heat maps may indicate areas of greatest concern, wherein red may represent a most critical factor that might suggest immediate intervention by a public housing authority to address a negative environmental factor, yellow may represent a less critical factor but one for which continued, close monitoring may be warranted, and green may represent less cause for concern.

The public housing index 156 configured as described herein may be used to allow public housing administrative personnel to determine how to address issues associated with improving the state of public housing, or to enable individuals living in public housing to transition out of public housing and to live more independently. Preferably, public housing evaluation unit 110 includes a user interface for public housing authorities 120, enabling public housing authority computers 180 to access public housing evaluation unit 110, and more particularly public housing index 156, to identify such interrelationships and to decide upon and implement measures to improve the physical environment of public housing residents. Preferably, user interface for public housing authorities 120 also enables such administrative public housing authorities to access individual digital public housing environment profiles to, in turn, allow direct intervention to be offered to specific public housing residents that the public housing authorities believe will improve the physical environment for such individual public housing resident, and/or allow direct intervention that will more quickly allow such public housing resident to transition out of public housing.

Figure 2:
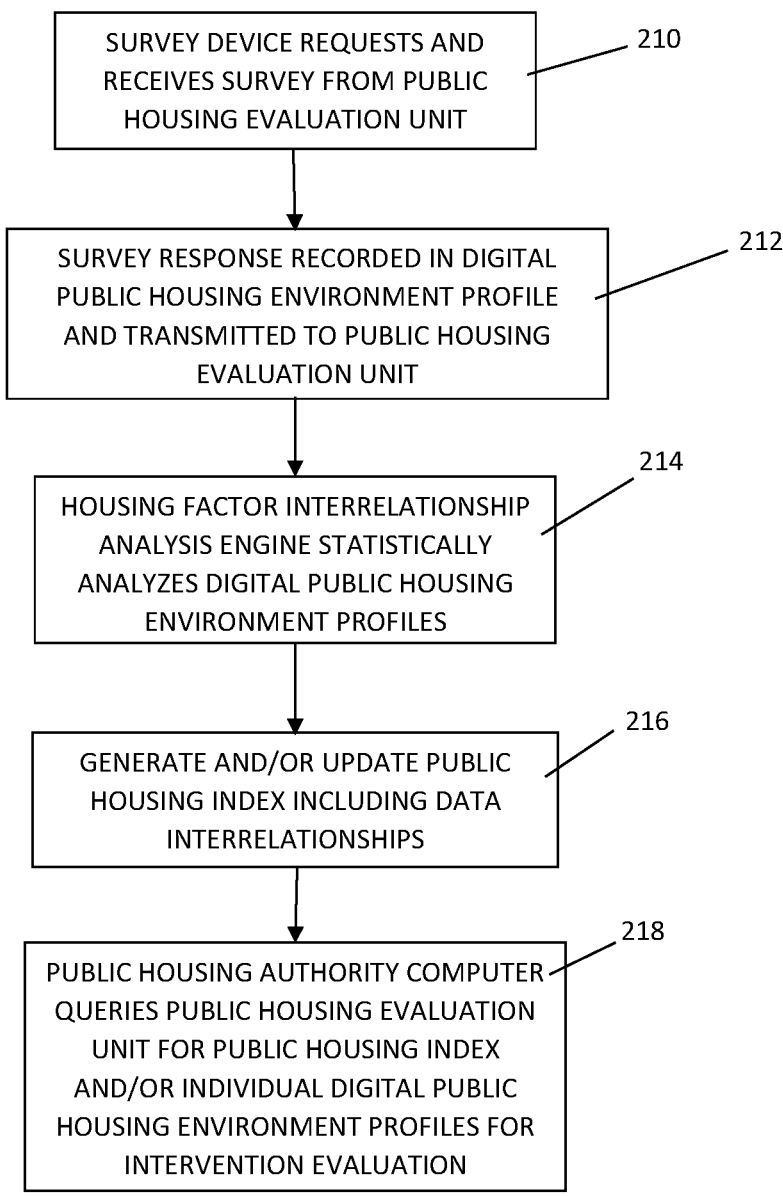
FIG. 2 is a schematic flowchart of a method for public housing evaluation in accordance with further aspects of an embodiment of the invention.

Next, FIG. 2 is a schematic view of a computer-implemented process for public housing evaluation in accordance with further aspects of an embodiment. At step 210, an authenticated user of survey device 150 causes survey device 150 to request a survey 114 from public housing evaluation unit 110, which survey 114 is then transmitted to survey device 150 for administering the survey to a public housing resident, a public housing agency member, an academic member, or a policy maker. Next at step 212, the survey participant's responses to survey 114 are recorded in a digital public housing environment profile which is transmitted from survey device 150 to public housing evaluation unit 110. At step 214, housing factor interrelationship analysis engine 118 analyzes the digital public housing environment profile along with other stored digital public housing environment profiles of other survey participants, and at step 216 generates and/or updates public housing index 156, including any interrelationships that were statistically identified among the factors in the digital public housing environment profiles. At step 218, a public housing authority computer 180 queries public housing evaluation unit 110 to review public housing index 156, and/or to obtain the individual digital public housing environment profile of a particular public housing resident so that they may evaluate whether any intervention may improve that public housing resident's physical environment, and/or improve their likelihood and/or preparedness for transitioning out of public housing.

Figure 3:
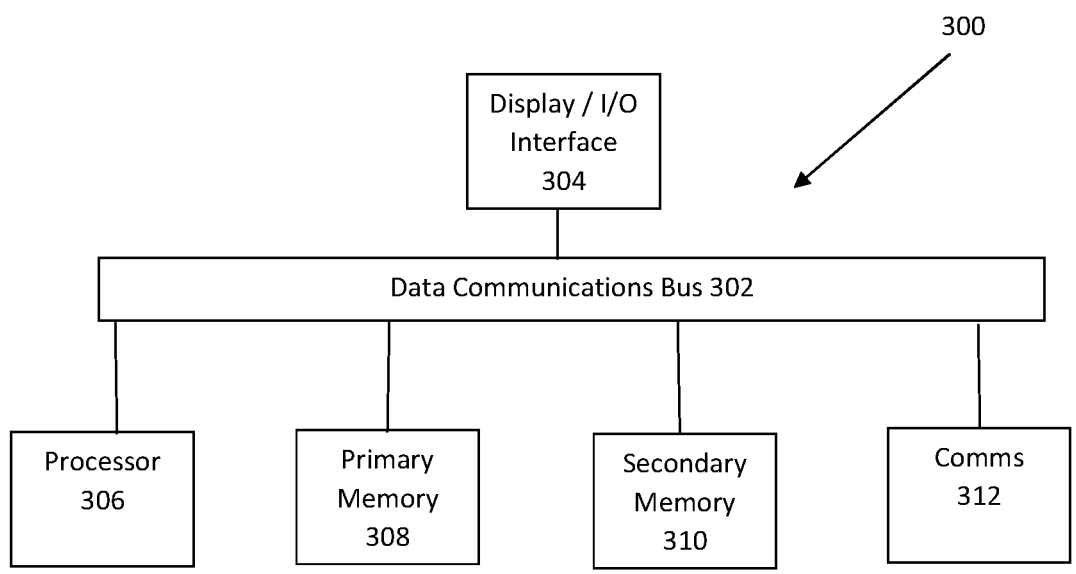
FIG. 3 is a schematic view of a computing device for use with the system of FIG. 1.

Those skilled in the art will recognize that each of public housing evaluation unit 110, survey device 150, and public housing authority computers 180 may each take the form of computer system 300 as reflected in FIG. 3, though variations thereof may readily be implemented by persons skilled in the art as may be desirable for any particular installation. In each such case, one or more computer systems 300 may carry out the foregoing methods as computer code.

Computer system 300 includes a communications bus 302, or other communications infrastructure, which communicates data to other elements of computer system 300. For example, communications bus 302 may communicate data (e.g., text, graphics, video, other data) between bus 302 and an I/O interface 304, which may include a display, a data entry device such as a keyboard, touch screen, mouse, or the like, and any other peripheral devices capable of entering and/or viewing data as may be apparent to those skilled in the art. Further, computer system 300 includes a processor 306, which may comprise a special purpose or a general purpose digital signal processor. Still further, computer system 300 includes a primary memory 308, which may include by way of non-limiting example random access memory ("RAM"), read-only memory ("ROM"), one or more mass storage devices, or any combination of tangible, non-transitory memory. Still further, computer system 300 includes a secondary memory 310, which may comprise a hard disk, a removable data storage unit, or any combination of tangible, non-transitory memory. Finally, computer system 300 may include a communications interface 312, such as a modem, a network interface (e.g., an Ethernet card or cable), a communications port, a PCMCIA slot and card, a wired or wireless communications system (such as Wi-Fi, Bluetooth, Infrared, and the like), local area networks, wide area networks, intranets, and the like.

Each of primary memory 308, secondary memory 310, communications interface 312, and combinations of the foregoing may function as a computer usable storage medium or computer readable storage medium to store and/or access computer software including computer instructions. For example, computer programs or other instructions may be loaded into the computer system 300 such as through a removable data storage device (e.g., a floppy disk, ZIP disks, magnetic tape, portable flash drive, optical disk such as a CD, DVD, or Blu-ray disk, Micro Electro Mechanical Systems ("MEMS"), and the like). Thus, computer software including computer instructions may be transferred from, e.g., a removable storage or hard disc to secondary memory 310, or through data communication bus 302 to primary memory 308.

Communication interface 312 allows software, instructions and data to be transferred between the computer system 300 and external devices or external networks. Software, instructions, and/or data transferred by the communication interface 312 are typically in the form of signals that may be electronic, electromagnetic, optical or other signals capable of being sent and received by communication interface 312. Signals may be sent and received using a cable or wire, fiber optics, telephone line, cellular telephone connection, radio frequency ("RF") communication, wireless communication, or other communication channels as will occur to those of ordinary skill in the art.

Computer programs, when executed, allow processor 306 of computer system 300 to implement the methods discussed herein for predictive risk assessment and intervention according to computer software including instructions.

Computer system 300 may perform any one of, or any combination of, the steps of any of the methods described herein. It is also contemplated that the methods according to the present invention may be performed automatically, or may be accomplished by some form of manual intervention.

The computer system 300 of FIG. 3 is provided only for purposes of illustration, such that the invention is not limited to this specific embodiment. Persons having ordinary skill in the art are capable of programming and implementing the instant invention using any computer system.

Further, computer system 300 may, in certain implementations, comprise a handheld device and may include any small-sized computing device, including by way of non-limiting example a cellular telephone, a smartphone or other smart handheld computing device, a personal digital assistant, a laptop or notebook computer, a tablet computer, a hand held console, an MP3 player, or other similarly configured small-size, portable computing device as may occur to those skilled in the art.

The system of FIG. 1 may, in an exemplary configuration, alternatively be implemented in a cloud computing environment for carrying out the methods described herein. That cloud computing environment uses the resources from various networks as a collective virtual computer, where the services and applications can run independently from a particular computer or server configuration making hardware less important. The cloud computer environment includes at least one survey device 150 operating as a client computer. The client computer may be any device that may be used to access a distributed computing environment to perform the methods disclosed herein, and may include (by way of non-limiting example) a desktop computer, a portable computer, a mobile phone, a personal digital assistant, a tablet computer, or any similarly configured computing device. That client computer preferably includes memory such as RAM, ROM, one or more mass storage devices, or any combination of the foregoing. The memory functions as a computer readable storage medium to store and/or access computer software and/or instructions.

That client computer also preferably includes a communications interface, such as a modem, a network interface (e.g., an Ethernet card), a communications port, a PCMCIA slot and card, wired or wireless systems, and the like. The communications interface allows communication through transferred signals between the client computer and external devices including networks such as the Internet and a cloud data center. Communication may be implemented using wireless or wired capability, including (by way of non-limiting example) cable, fiber optics, telephone line, cellular telephone, radio waves or other communications channels as may occur to those skilled in the art.

Such client computer establishes communication with the one more servers via, for example, the Internet, to in turn establish communication with one or more cloud data centers that implement public housing evaluation system 100. A cloud data center may include one or more networks that are managed through a cloud management system. Each such network includes resource servers that permit access to a collection of computing resources and components of public housing evaluation system 100, which computing resources and components can be invoked to instantiate a virtual computer, process, or other resource for a limited or defined duration. For example, one group of resource servers can host and serve an operating system or components thereof to deliver and instantiate a virtual computer. Another group of resource servers can accept requests to host computing cycles or processor time, to supply a defined level of processing power for a virtual computer. Another group of resource servers can host and serve applications to load on an instantiation of a virtual computer, such as an email client, a browser application, a messaging application, or other applications or software.

The cloud management system may comprise a dedicated or centralized server and/or other software, hardware, and network tools to communicate with one or more networks, such as the Internet or other public or private network, and their associated sets of resource servers. The cloud management system may be configured to query and identify the computing resources and components managed by the set of resource servers needed and available for use in the cloud data center. More particularly, the cloud management system may be configured to identify the hardware resources and components such as type and amount of processing power, type and amount of memory, type and amount of storage, type and amount of network bandwidth and the like, of the set of resource servers needed and available for use in the cloud data center. The cloud management system can also be configured to identify the software resources and components, such as type of operating system, application programs, etc., of the set of resource servers needed and available for use in the cloud data center.

In accordance with still further aspects of an embodiment of the invention, a computer program product may be provided to provide software to the cloud computing environment. Computer products store software on any computer useable medium, known now or in the future. Such software, when executed, may implement the methods according to certain embodiments of the invention. By way of non-limiting example, such computer usable mediums may include primary storage devices (e.g., any type of random access memory), secondary storage devices (e.g., hard drives, floppy disks, CD ROMS, ZIP disks, tapes, magnetic storage devices, optical storage devices, MEMS, nanotech storage devices, etc.), and communication mediums (e.g., wired and wireless communications networks, local area networks, wide area networks, intranets, etc.). Those skilled in the art will recognize that the embodiments described herein may be implemented using software, hardware, firmware, or combinations thereof.

The cloud computing environment described above is provided only for purposes of illustration and does not limit the invention to this specific embodiment. It will be appreciated that those skilled in the art are readily able to program and implement the invention using any computer system or network architecture.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:

1. A computer-implemented method for evaluating public housing, the computer-implemented method performed by a public housing evaluation unit having a processor and a memory, the computer-implemented method comprising:

receiving, by the processor from a remote survey device, a digital public housing profile associated with a human survey participant, wherein the digital public housing profile comprises physical environment characteristics and demographic data of the human survey participant correlated with public housing data that is maintained in a public housing database;

mapping, by the processor, the physical environment characteristics and the demographic data from the digital public housing profile to standardized public housing data in a public housing index, wherein the standardized public housing data is categorized in the public housing index by public housing environmental factors, and wherein the public housing index comprises a plurality of digital public housing profiles aggregated over a common time period;

identifying, by the processor, a target factor of the public housing environmental factors in the digital public housing profile;

assigning, by the processor, a numeric value to the target factor based on a non-numeric category in the digital public housing profile matching a category in the public housing index;

scoring, by the processor, the numeric value based on strength of one or more interrelationships between the digital public housing profile and the standardized public housing data;

weighting, by the processor, the numeric value according to an expected impact of the target factor to the public housing of the human survey participant based on a historical subset of the standardized public housing data;

filtering, by the processor, the public housing environmental factors that have numeric values with a weighted score above a threshold for implementing an intervention;

outputting, by the processor to a graphical user interface of the public housing evaluation unit, one or more intervention activities to address the public housing environmental factors that have numeric values with a weighted score above the threshold with a prediction of updated interrelationships between the digital public housing profile and the standardized public housing data; and storing, by the processor in the memory, an updated public housing index including the updated interrelationships after the one or more intervention activities have been implemented.

2. The computer-implemented method of claim 1, wherein the digital public housing profile further comprises data indicative of the human survey participant's observation of one or more of (i) crime impacting a particular public housing facility, (ii) overall health of residents of a particular public housing facility or individual housing unit, (iii) physical environment of the particular public housing facility or individual housing unit, (iv) aging of building infrastructure for the particular public housing facility or individual housing unit, (v) cleanliness of the particular public housing facility or individual housing unit, (vi) intergenerational relationships among residents, (vii) education levels of residents, and (viii) employment status of residents.

3. The computer-implemented method of claim 1, further comprising receiving, at the processor, a query from a public housing authority computer for viewing access to the public housing index.

4. The computer-implemented method of claim 3, further comprising, in response to receiving the query from the public housing authority computer, transmitting at least a portion of the public housing index for display on the public housing authority computer.

5. The computer-implemented method of claim 1, further comprising receiving a query from a public housing authority computer for an individual digital public housing profile of the public housing index.

6. The computer-implemented method of claim 5, further comprising, in response to receiving the query from the public housing authority computer of an individual digital public housing profile, transmitting the individual digital public housing profile for display on the public housing authority computer.

7. A system for evaluating public housing, the system comprising:

a public housing evaluation unit having a processor and a memory; and a remote survey device in data communication with the public housing evaluation unit, wherein the memory stores computer-executable instructions that, when executed by the processor, causes the system to:

receive, from the remote survey device, a digital public housing profile associated with a human survey participant, wherein the digital public housing profile comprises physical environment characteristics and demographic data of the human survey participant correlated with public housing data that is maintained in a public housing database;

map the physical environment characteristics and the demographic data from the digital public housing profile to standardized public housing data in a public housing index, wherein the standardized public housing data is categorized in the public housing index by public housing environmental factors, and wherein the public housing index comprises a plurality of digital public housing profiles aggregated over a common time period;

identify a target factor of the public housing environmental factors in the digital public housing profile;

assign a numeric value to the target factor based on a non-numeric category in the digital public housing profile matching a category in the public housing index;

score the numeric value based on strength of one or more interrelationships between the digital public housing profile and the standardized public housing data;

weight the numeric value according to an expected impact of the target factor to the public housing of the human survey participant based on a historical subset of the standardized public housing data;

filter the public housing environmental factors that have numeric values with a weighted score above a threshold for implementing an intervention;

output, to a graphical user interface of the public housing evaluation unit, one or more intervention activities to address the public housing environmental factors that have numeric values with a weighted score above the threshold with a prediction of updated interrelationships between the digital public housing profile and the standardized public housing data; and store, in the memory, an updated public housing index including the updated interrelationships after the one or more intervention activities have been implemented.

8. The system of claim 7, wherein the digital public housing profile further comprises data indicative of the human survey participant's observation of one or more of (i) crime impacting a particular public housing facility, (ii) overall health of residents of a particular public housing facility or individual housing unit, (iii) physical environment of the particular public housing facility or individual housing unit, (iv) aging of building infrastructure for the particular public housing facility or individual housing unit, (v) cleanliness of the particular public housing facility or individual housing unit, (vi) intergenerational relationships among residents, (vii) education levels of residents, and (viii) employment status of residents.

9. The system of claim 7, wherein the computer-executable instructions, when executed by the processor, further cause the system to receive, from a public housing authority computer, a query for viewing access to the public housing index.

10. The system of claim 9, wherein the computer-executable instructions, when executed by the processor, further cause the system to, in response to receiving the query from the public housing authority computer, transmit at least a portion of the public housing index for display on the public housing authority computer.

11. The system of claim 7, wherein the computer-executable instructions, when executed by the processor, further cause the system to receive, from a public housing authority computer, a query for an individual digital public housing profile of the public housing index.

12. The system of claim 11, wherein the computer-executable instructions, when executed by the processor, further cause the system to, in response to the query from the public housing authority computer for an individual digital public housing profile, transmit the individual digital public housing profile for display on the public housing authority computer.

13. The system of claim 7, wherein the processor and the memory are implemented in a cloud computing environment, and wherein the remote survey device is in data communication with the public housing evaluation unit through the cloud computing environment.

14. A non-transitory computer-readable storage medium comprising instructions that, when executed by a processor of a public housing evaluation unit, cause the public housing evaluation unit to:

receive, from a remote survey device in data communication with the public housing evaluation unit, a digital public housing profile associated with a human survey participant, wherein the digital public housing profile comprises physical environment characteristics and demographic data of the human survey participant correlated with public housing data that is maintained in a public housing database;

map the physical environment characteristics and the demographic data from the digital public housing profile to standardized public housing data in a public housing index, wherein the standardized public housing data is categorized in the public housing index by public housing environmental factors, and wherein the public housing index comprises a plurality of digital public housing profiles aggregated over a common time period;

identify a target factor of the public housing environmental factors in the digital public housing profile;

assign a numeric value to the target factor based on a non-numeric category in the digital public housing profile matching a category in the public housing index;

score the numeric value based on strength of one or more interrelationships between the digital public housing profile and the standardized public housing data;

weight the numeric value according to an expected impact of the target factor to the public housing of the human survey participant based on a historical subset of the standardized public housing data;

filter the public housing environmental factors that have numeric values with a weighted score above a threshold for implementing an intervention;

output, to a graphical user interface of the public housing evaluation unit, one or more intervention activities to address the public housing environmental factors that have numeric values with a weighted score above the threshold with a prediction of updated interrelationships between the digital public housing profile and the standardized public housing data; and store, in memory of the public housing evaluation unit, an updated public housing index including the updated interrelationships after the one or more intervention activities have been implemented.

15. The non-transitory computer-readable storage medium of claim 14, wherein the digital public housing profile further comprises data indicative of the human survey participant's observation of one or more of (i) crime impacting a particular public housing facility, (ii) overall health of residents of a particular public housing facility or individual housing unit, (iii) physical environment of the particular public housing facility or individual housing unit, (iv) aging of building infrastructure for the particular public housing facility or individual housing unit, (v) cleanliness of the particular public housing facility or individual housing unit, (vi) intergenerational relationships among residents, (vii) education levels of residents, and (viii) employment status of residents.

16. The non-transitory computer-readable storage medium of claim 14, wherein the instructions, when executed by the processor, further cause the public housing evaluation unit to receive, from a public housing authority computer, a query for viewing access to the public housing index.

17. The non-transitory computer-readable storage medium of claim 16, wherein the instructions, when executed by the processor, further cause the public housing evaluation unit to, in response to receiving the query from the public housing authority computer, transmit at least a portion of the public housing index for display on the public housing authority computer.

18. The non-transitory computer-readable storage medium of claim 14, wherein the instructions, when executed by the processor, further cause the public housing evaluation unit to receive, from a public housing authority computer, a query for an individual digital public housing profile of the public housing index.

19. The non-transitory computer-readable storage medium of claim 18, wherein the instructions, when executed by the processor, further cause the public housing evaluation unit to, in response to the query from the public housing authority computer for an individual digital public housing profile, transmit the individual digital public housing profile for display on the public housing authority computer.

20. The non-transitory computer-readable storage medium of claim 14, wherein the instructions, when executed by the processor, further cause the public housing evaluation unit to provide, via the graphical user interface, an interface for administration and collection of a digital survey by which the public housing evaluation unit:

receives a login request from the remote survey device;
authenticates the login request;
receives a request from the remote survey device for the digital survey from a survey database; and
transmits the digital survey to the remote survey device for administering to the human survey participant,
wherein changes to the digital survey are correlated to the updated public housing index.

\* \* \* \* \*